United States Patent [19]

Harris

[11] Patent Number: 5,418,305
[45] Date of Patent: May 23, 1995

[54] ESTER-FUNCTIONAL MONOMERS AND POLYMERS PREPARED FROM SAME

[75] Inventor: Rodney M. Harris, Chicago, Ill.

[73] Assignee: The Sherwin-Williams Company, Cleveland, Ohio

[21] Appl. No.: 307,136

[22] Filed: Sep. 16, 1994

Related U.S. Application Data

[62] Division of Ser. No. 176,609, Jan. 3, 1994, Pat. No. 5,349,080.

[51] Int. Cl.⁶ .................................. C08F 118/02
[52] U.S. Cl. ........................................ 526/319
[58] Field of Search ........................... 526/319

[56] References Cited

U.S. PATENT DOCUMENTS

| | | | |
|---|---|---|---|
| 3,594,415 | 7/1971 | Zisman et al. | 260/515 |
| 3,803,254 | 4/1974 | Hattori et al. | 260/669 |

FOREIGN PATENT DOCUMENTS 0723674 12/1965 Canada ........................... 260/479

*Primary Examiner*—Joseph L. Schofer
*Assistant Examiner*—N. Sarofim
*Attorney, Agent, or Firm*—Robert E. McDonald; Steven W. Tan; Heidi A. Boehlefeld

[57] ABSTRACT

An unsaturated ester monomer having the structure:

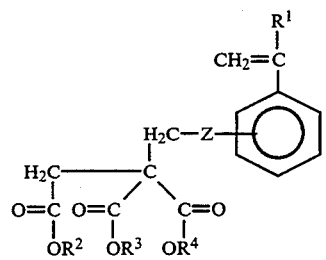

wherein $R^1$ is hydrogen or methyl; $R^2$, $R^3$ and $R^4$ are each independently lower alkyl of 1 to about 4 carbons; and Z is nothing or is a divalent radical having 1 to about 20 carbons.

7 Claims, No Drawings

ESTER-FUNCTIONAL MONOMERS AND POLYMERS PREPARED FROM SAME

This is a divisional of application Ser. No. 08/176,609, filed on Jan. 03, 1994, (now U.S. Pat. No. 5,349,080).

BACKGROUND OF THE INVENTION

1. Field of the Invention

This invention involves novel polymerizable monomers having pendent ester groups and polymers prepared from those monomers. The monomers have the structure:

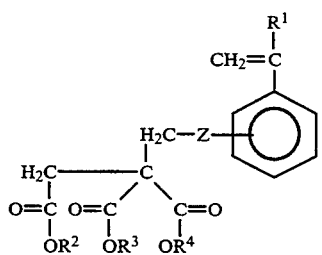

wherein $R^1$ is hydrogen or methyl; $R^2$ $R^3$ and $R^4$ are each independently lower alkyl of 1 to about 4 carbons; and Z is nothing or is a divalent alkyl radical having 1 to about 20 carbon atoms. Preferred divalent alkyl radicals are methylene chains —(—CH$_2$—)$_n$— wherein n is 1 to 20.

This invention also relates to polymers obtained by polymerizing, under free radical addition polymerization conditions, (i) the unsaturated ester monomer of this invention; and (ii) optionally, at least one other unsaturated monomer copolymerizable with the unsaturated ester monomer. The monomers are also useful as reactive diluents and as precursors for acid and/or anhydride-functional monomers.

2. Description of the Prior Art

Unsaturated, polymerizable esters, such as butyl acrylate, methyl methacrylate, methyl crotonate, or ethyl tiglate and polymers or copolymers incorporating these materials are known in the art. By the selection of one or more of these esters, the characteristics of a polymer may be tailored to provide a desired glass transition temperature, hardness, flexibility or other desired property. The prior art has not, however, taught polymers obtained by the polymerization of the novel styrene-based ester monomers of this invention.

BRIEF SUMMARY OF THE INVENTION

This invention involves polymerizable unsaturated monomers having pendent ester functionality, and to polymers derived by polymerizing the ester monomer through its unsaturation either as a homopolymer or, preferably, in combination with one or more additional copolymerizable monomers. The esters of this invention can be utilized to alter the glass transition temperature, solubility, hardness, flexibility, crystalinity or other physical or performance property of a copolymer by incorporating these novel monomers into the polymer backbone by free radical polymerization. Furthermore, since the unsaturated esters of this invention are styrene based materials, their reactivity ratios with other polymerizable monomers such as styrene and (meth)acrylate monomers under free radical polymerization conditions will be different than the reactivity ratios of the common prior art (meth)acrylate esters with those same copolymerizable monomers. Therefore, the monomers of this invention can provide a way to incorporate ester side chains while altering the arrangement of other monomers along the polymeric backbone compared to the use of the common prior art unsaturated esters. Additionally, since the ester groups of the monomer can be, if desired, fully or partially hydrolyzed, either before or after polymerization to produce acid-functional monomers and/or polymers, these ester monomers of this invention have special utility when utilized as precursors for those acid-functional materials.

Accordingly, one object of this invention is to provide novel styrene based ester monomers. Another object is to provide polymers and copolymers incorporating the ester monomers. Another object is to provide new unsaturated esters which are readily hydrolyzable to acid functionality. These and other objects of the invention will become apparent from the following discussions.

DETAILED DESCRIPTION OF THIS INVENTION

The unsaturated styrene based ester monomers of this invention can be conveniently prepared by the reaction of the anion of a trialkyl-1,1,2-ethanetricarboxylate (such as triethyl-1,1,2-ethanetricarboxylate), with a vinyl benzene alkyl halide (such as vinyl benzyl chloride).

The vinyl benzene alkyl halide has the general structure:

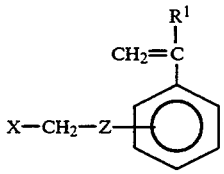

wherein $R^1$ and Z are as defined above and X is a halogen atom. The vinyl benzene alkyl halides of various lengths of Z can be readily prepared by a variety of methods known in the art. For example, Grignard reaction synthesis of the vinyl benzene alkyl halides are representatively set forth in M. L. Hallensleben, *Angew. Makronol. Chem.*, 31 147 (1973), and Montheard et al. *J. Polym. Sci. Part A., Polym. Chem.*, 27 (8), 2539 (1989). For cost and availability of starting materials, it is especially preferred that Z be nothing or be lower alkyl of 1 to about 4 carbons. Vinyl benzyl chloride, where Z is nothing, $R^1$ is hydrogen and X is chlorine, is especially preferred.

The trialkyl-1,1,2-ethanetricarboxylate has the general structure:

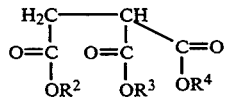

wherein $R^2$, $R^3$ and $R^4$ are lower alkyl of 1 to about 4 carbons. Due to cost and reactivity, triethyl-1,1,2-ethanetricarboxylate is especially preferred.

The reaction to produce the preferred ester-functional monomer is representatively shown below wherein the trialkyl-1,1,2-ethanetricarboxylate is triethyl-1,1,2-ethanetricarboxylate and the vinyl benzene alkyl halide is vinyl benzyl chloride:

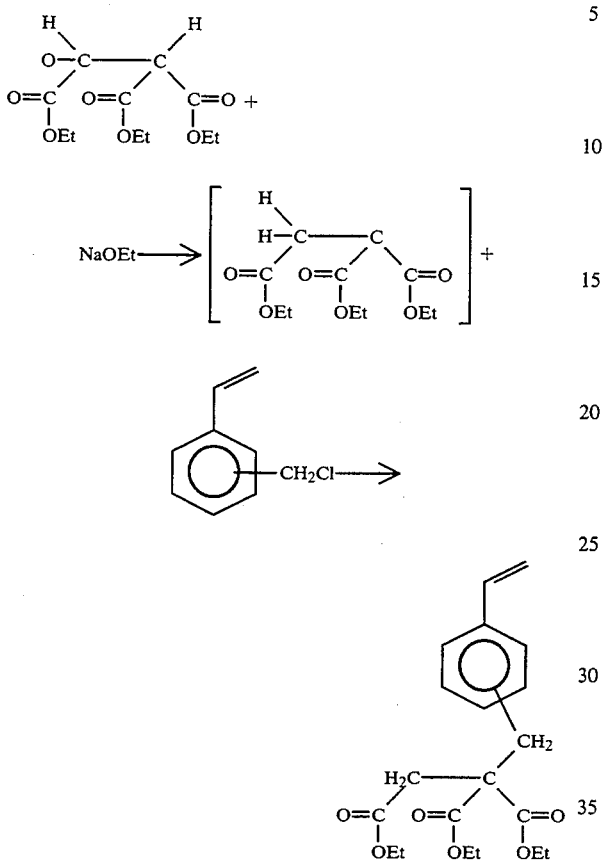

The preparation of the anion of the trialkyl-1,1,2-ethanetricarboxylate is conveniently accomplished by mixing ethanolic sodium ethoxide with the tricarboxylate and refluxing the solution for five to ten minutes. Typically the sodium ethoxide will be present at a level to provide about 0.8 to about 1.1 moles of sodium ethoxide for each mole of tricarboxylate. The anion of the tricarboxylate can then be reacted with the vinyl benzene alkyl halide by mixing the two materials in an approximately 1 to 1 mole ratio and by maintaining the reaction at reflux, in the presence of small amounts (e.g. 500 ppm of the total reaction mixture) of polymerization inhibitors, for 1 to about 3 hours to prepare the vinyl benzene alkyl-1,2-ethane tricarboxylate.

In one use of the monomer of the invention, the vinyl benzene alkyl-1,1,2-ethane tricarboxylate could be hydrolyzed to produce the corresponding tricarboxylic acid by reaction with base, such as sodium hydroxide or potassium hydroxide, followed by acidification. Alternatively, the hydrolysis can be accomplished by direct reaction of the tricarboxylate with aqueous acid such as aqueous hydrochloric acid. Base hydrolysis is generally preferred and can be readily conducted by admixing an aqueous and/or ethanolic solution of sodium hydroxide or potassium hydroxide and maintaining the reaction mixture at reflux until the reaction is complete (typically 3 to 5 hours). The salt product can be collected by filtration and the tricarboxylic acid is then generated by acidifying an aqueous solution of the salt to a pH less than about 3, typically by using dilute acid such as aqueous hydrochloric acid.

The polymerization of the novel monomers of this invention either alone or with other unsaturated copolymerizable monomers, such as acrylic or methacrylic monomers or styrene, proceeds at excellent yield and can produce polymers having excellent performance characteristics.

The polymers which incorporate the monomers of this invention could conveniently be prepared by polymerizing the styrene based ester monomer, and, normally, at least one other copolymerizable monomer under free radical addition polymerization conditions. Typically, the polymerization would be conducted in an inert solvent and in the presence of an initiator, such as a peroxide or azo compound, at temperatures ranging from 35° C. to about 200° C., and especially 75° C., to about 150° C. Representative initiators include di-t-butyl peroxide, cumene hydroperoxide, and azobis(isobutyronitrile).

The mixture of monomers used to prepare the polymers would typically comprise from 1 to about 100, and especially 5 to about 85 percent by weight of the styrene based ester monomer. The remainder of the mixture of monomers would be comprised of at least one other unsaturated monomer copolymerizable with the styrene based ester monomer. If it is desired to generate a reactive polymer, suitable unsaturated monomers containing potentially reactive sites such as hydroxy, epoxy, acid or amine groups can be incorporated into the polymer along with the styrene based esters. Typically, the styrene based ester monomers would be copolymerized with one or more monomers having ethylenic unsaturation such as:

(i) acrylic, methacrylic, crotonic, tiglic, or other unsaturated acids or derivatives thereof, such as: acrylic acid, methacrylic acid, methyl acrylate, ethyl acrylate, propyl acrylate, isopropyl acrylate, butyl acrylate, isobutyl acrylate, ethylhexyl acrylate, amyl acrylate, 3,5,5 -trimethylhexyl acrylate, methyl methacrylate, ethyl methacrylate, propyl methacrylate, dimethylaminoethyl methacrylate, isobornyl methacrylate, ethyl tiglate, methyl crotonate, ethyl crotonate, 2-hydroxyethyl acrylate, 2-hydroxyethyl methacrylate, 2-hydroxypropyl acrylate, 4-hydroxybutyl methacrylate, 2-hydroxypropyl methacrylate, 3-hydroxybutyl acrylate, 4-hydroxypentyl acrylate, 2-hydroxyethyl ethacrylate, 3-hydroxybutyl methacrylate, 2-hydroxyethyl chloroacrylate, diethylene glycol methacrylate, glycidyl acrylate, glycidyl methacrylate, tetra ethylene glycol acrylate, etc.;

(ii) vinyl compounds such as vinyl acetate, vinyl propionate, vinyl butyrate, vinyl isobutyrate, vinyl benzoate, vinyl m-chlorobenzoate, vinyl p-methoxybenzoate, vinyl α-chloroacetate, vinyl toluene, vinyl chloride, paravinyl benzyl alcohol, etc.;

(iii) styrene-based materials such as styrene, α-methyl styrene, α-ethyl styrene, α-bromo styrene, 2,6-dichlorostyrene, etc.;

(iv) allyl compounds such as allyl chloride, allyl acetate, allyl benzoate, allyl methacrylate, etc.;

(v) other copolymerizable unsaturated monomers such as ethylene, acrylonitrile, methacrylonitrile, dimethyl maleate, isopropenyl acetate, isopropenyl isobutyrate, acrylamide, methacrylamide, and dienes such as 1,3-butadiene, etc.

The free radical addition polymers of this invention could typically be used as lacquers or as reactive polymers and would have application in adhesives, coatings, inks, plastics, chemical additives and fibers. Where the polymers are required to be of the reactive crosslinking type, suitable functional monomers which can be used include acrylic or methacrylic acid, hydroxy ethyl acrylate, 2-hydroxy propyl methacrylate, glycidyl acrylate, tertiary-butyl amino ethyl methacrylate, etc. The polymer may, in such a case, be used in combination with a crosslinking agent which would be reactive with the functional groups of the polymer. Typical crosslinking agents would include polyisocyanates, polyepoxides or nitrogen resins such as the condensates of an aldehyde such as formaldehyde with a nitrogenous compound such as urea, melamine or benzoguanamine or a lower alkyl ether of such a condensate.

The following examples have been selected to illustrate specific embodiments and practices of advantage to a more complete understanding of the invention. Unless otherwise stated, "parts" means parts-by-weight and "percent" is percent-by-weight. The starting raw materials utilized in these examples are commercially available. The vinyl benzyl chloride is a 70/30 meta/para isomer commercially available from Dow Chemical Company. The sodium metal, diethyl malonate, ethyl chloroacetate, acetic anhydride, butylated hydroxy toluene, and, unless otherwise indicated, the triethyl-1,1,2-ethanetricarboxylate, were obtained from Aldrich Chemical Company. The absolute ethanol was obtained from USI-Quantum Chemical Company.

EXAMPLE A

Triethyl-1,1,2,-ethane tricarboxylate

A solution of sodium ethoxide in ethanol was prepared by slowly adding 559.4 g sodium metal into 7890 g of absolute ethanol. Next, 3891.9 g of diethyl malonate was added to the ethanol solution over 45 minutes at an initial temperature of 25° C. The mixture was homogenized by heating at 50° C. for 40 minutes. Next, 3000 g ethyl chloroacetate was slowly added over approximately 90 minutes, while the reaction mixture was maintained at 40°-50° C. with occasional warming. The mixture was then heated at reflux for 2 hours, then cooled to room temperature.

The mixture was worked-up by stripping off approximately two-thirds of the ethanol (~750-800 ml). The residue was then washed with water and extracted with toluene. The toluene solution was dried over magnesium sulfate, followed by removal of the toluene to give a dark red residue. The product residue was distilled under reduced pressure to give 3252 g (approximately 54.3% yield) of triethyl-1,1,2-ethane tricarboxylate in ~97% purity.

EXAMPLE B

Triethyl 1-(3/4-vinyl benzyl)-1,1,2-ethane tricarboxylate

An ethanol solution of sodium ethoxide was prepared by adding 283 g of sodium metal over 8 hours to 6404 g of ethanol (maximum temperature 60° C.). Triethyl-1,1,2-ethane tricarboxylate (Example A, 3156.9 g) was then added over 20 minutes to the ethanol solution (maximum temperature 30° C.). The mixture was then heated at reflux for 5-10 minutes, then cooled to 25° C. Next, 1816.3 g of vinyl benzyl chloride was added over 40 minutes, while keeping the temperature under 35° C. A small amount of butylated hydroxy toluene inhibitor was added. The mixture was heated at reflux for 2 hours and 20 minutes and then allowed to cool to room temperature.

The reaction mixture was neutralized (pH~7) with glacial acetic acid, and approximately two-thirds of the ethanol was stripped off under reduced pressure. Sodium chloride was filtered off. The unpurified styryl methylene triester/ethanol solution (63.6% NVM in ethanol) was then utilized to produce the corresponding tricarboxylic acid as shown in Example E.

EXAMPLE C

Triethyl 1-(3/4-vinyl benzyl)-1,2-ethane tricarboxylate

A sodium ethoxide/ethanol solution was prepared by slowly adding 16.02 g of sodium metal to 365 g of absolute ethanol with slow stirring. The mixture was then heated at reflux for 5-10 minutes. Triethyl-1,1,2-ethane tricarboxylate (180 g from Aldrich Chemical Company) was added over 20 minutes to the mixture at room temperature. The mixture was heated at reflux for 5-10 minutes, then cooled to 25° C. Next, 112.9 g of vinyl benzyl chloride was added over 20 minutes (maximum temperature of the reaction mixture was 45° C. ). A small amount of butylated hydroxy toluene inhibitor was added. The mixture was heated to reflux for 2 hours, then cooled to room temperature.

The reaction mixture was neutralized (pH~7) with glacial acetic acid. About two-thirds of the ethanol was stripped off under reduced pressure. Six hundred sixty-five milliliters of deionized water was added and the product was extracted with toluene. The combined toluene extracts were dried over sodium sulfate. Removing the volatiles with rotary evaporation produced 255.2 g of triethyl-1-(3/4-vinyl benzyl)-1,1,2-ethane tricarboxylate as a yellow liquid in an isolated yield of 96% of theory. NMR and infrared spectral data confirmed the structure of the tricarboxylate product.

One potential utility for the styrene based ester monomers of this invention is their use as precursors for acid-functional monomers and polymers. Acid-functional monomers and polymers are useful for their reactivity with other groups such as hydroxyl or epoxy and also can be neutralized with a base such as ammonia to provide water dispersibility. Example D and E show the production of such acid-functional monomers.

EXAMPLE D

1-(3/4-Vinyl benzyl)-1,1,2-ethane tricarboxylic acid

An aqueous/ethanolic potassium hydroxide solution was prepared by slowly mixing 2805 ml of absolute ethanol and 147.5 ml of deionized water. A small amount of butylated hydroxy toluene inhibitor was added. Potassium hydroxide (363 g) was added slowly keeping the temperature below reflux. The mixture was then cooled to 30° C. and 240 g, (approximately 0.662 tool) of the crude product of the vinyl benzyl triester of Example C was quickly added. The mixture rapidly turned cloudy and then became homogeneous upon heating to reflux. An additional small amount of butylated hydroxy toluene inhibitor was again added and reflux continued for 4 hours. The precipitate laden mixture was then allowed to cool to room temperature. The tricarboxylate salt was collected by suction filtration, then dissolved in deionized water (800 ml) and neutralized with dilute aqueous hydrochloric acid (5:1 conc. HCl/H$_2$O vol. ratio) to a pH<2. Two additions of approximately 3000 ml each of anhydrous acetone was added to the acidified solution and the potassium chloride precipitate was filtered off. The acetone was then stripped off and the process was then repeated. The remaining volatiles were then removed under reduced pressure to give an isolated yield of 113.1 g (74.4%) of an off white solid (mp 112.5°–125° C. decomposed). NMR, infrared and acid dissociation constants data were used to characterize the tricarboxylic acid product. In water, aqueous potassium hydroxide titration identified the Pka's of the three carboxylic acid groups as 2.60; 4.59 and 8.06.

EXAMPLE E 1-(3/4-Vinyl benzyl)-1,1,2-ethane tricarboxylic acid

An aqueous potassium hydroxide solution (6126 g, 109.2 mol of potassium hydroxide in 2490 g of water) was slowly added to 6375 g (11.17 mol) of the unpurified vinyl benzyl triester/ethanol solution of Example B, (36.47% NVM) containing a small amount of butylated hydroxy toluene inhibitor, while keeping the exothermic reaction below reflux. An additional small amount of butylated hydroxy toluene was again added. The mixture was then heated to reflux for 4 hours, and cooled to room temperature. The precipitated solid tricarboxylate salt was collected by filtration. Additional ethanol (12000 g) and then propanol (12000 g) were used to precipitate out the remaining salt which was collected by filtration.

A dispersion of the tricarboxylate salt was made in anhydrous acetone. The salt was neutralized by acidifying the mixture with a concentrated hydrochloric acid (HCl)/water solution (5:1 volume ratio) to a pH of <2. The acetone, aqueous HCl solution was then treated with a 2:1 hexane/toluene mixture. Stripping volatiles from the residual solution yielded 2777 g of an orange solid crude product. NMR and infrared spectral data confirmed the structure as the desired tricarboxylate. The product also contained some neutralized potassium carboxylate salt.

Another potential utility of the ester monomers of this invention is their use as polymerizable components of free radical addition polymers. A theoretical production of such a polymer is given in Example F.

EXAMPLE F

HYDROXY-FUNCTIONAL COPOLYMER

A representative hydroxy-functional polymer incorporating the styrene based ester of this invention could be prepared, in a representative fashion, as follows:

A reaction vessel equipped with a mechanical stirrer, water cooled condenser, nitrogen inlet, water trap, thermometer and heating mantel could be charged with 172.5 parts of n-butyl acetate and heated to approximately 230° F. and a monomer premix comprising 91.2 parts of methyl methacrylate, 58 parts of butyl acrylate, 58 parts of hydroxy ethyl methacrylate, 15 parts of the monomer of Example C, 54 parts styrene and an initiator premixture composed of 11.5 parts of n-butyl acetate and 5.7 parts of 2,2'-azobis(2-methylbutyronitrile) could be metered simultaneously into the polymerization reactor at a constant rate for approximately 4 hours. The reaction temperature could be maintained for an additional 2 hours after the addition was completed and then allowed to cool to yield the hydroxy-functional acrylic polymer incorporating the styrene based ester of this invention. Such a hydroxy-functional polymer could be utilized in combination with a typical crosslinking agent, such as a polyisocyanate or a melamine curing agent to provide curable coating compositions.

While this invention has been described by a specific number of embodiments, other variations and modifications may be made without departing from the spirit and scope of the invention as set forth in the appended claims.

The invention claimed is:

1. A polymer which comprises the free radical polymerization reaction product of:
   (i) 1% to 100% by weight of an unsaturated ester monomer having the structure:

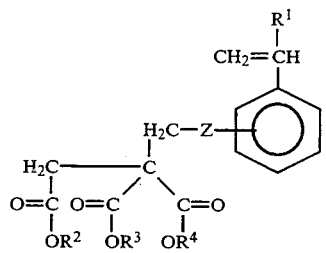

wherein $R^1$ is hydrogen or methyl; $R^2$, $R^3$ and $R^4$ are each independently lower alkyl of to about 4 carbons; and Z is nothing or is a divalent radical having 1 to about 20 carbons; and
   (ii) 0% to 99% by weight of at least one other unsaturated monomer copolymerizable with the unsaturated ester-functional monomer.

2. The polymer of claim 1 wherein $R^1$ is hydrogen.

3. The polymer of claim 1 wherein $R^1$ is methyl.

4. The polymer of claim 1 wherein $R^2$, $R^3$ and $R^4$ are each ethyl.

5. The polymer of claim 1 wherein Z is nothing.

6. The polymer of claim 1 wherein Z is a divalent polymethylene chain —(—$CH_2$—)$_n$—wherein n is 1 to 20.

7. The polymer of claim 1 wherein the polymer comprises the reacting product of 5% to 85% by weight of the unsaturated ester monomer and 15% to 95% of at least one other unsaturated monomer copolymerizable with the unsaturated ester-functional monomer.

* * * * *